(12) United States Patent
Ozawa et al.

(10) Patent No.: US 12,213,665 B2
(45) Date of Patent: Feb. 4, 2025

(54) METHODS FOR CLOSING A WOUND

(71) Applicant: OLYMPUS MEDICAL SYSTEMS CORP., Tokyo (JP)

(72) Inventors: Keita Ozawa, Hino (JP); Kunihide Kaji, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 147 days.

(21) Appl. No.: 17/558,691

(22) Filed: Dec. 22, 2021

(65) Prior Publication Data
US 2022/0240934 A1 Aug. 4, 2022

Related U.S. Application Data

(60) Provisional application No. 63/145,546, filed on Feb. 4, 2021.

(51) Int. Cl.
*A61B 17/06* (2006.01)
*A61B 17/00* (2006.01)
*A61B 17/04* (2006.01)

(52) U.S. Cl.
CPC .... *A61B 17/06166* (2013.01); *A61B 17/0469* (2013.01); *A61B 2017/00269* (2013.01);
(Continued)

(58) Field of Classification Search
CPC .......... A61B 17/06166; A61B 17/0469; A61B 2017/00269; A61B 2017/00818;
(Continued)

(56) References Cited

U.S. PATENT DOCUMENTS

| | | | |
|---|---|---|---|
| 2003/0074023 A1* | 4/2003 | Kaplan | A61B 17/1146 606/228 |
| 2007/0112362 A1* | 5/2007 | Mikkaichi | A61B 17/0487 606/153 |

(Continued)

FOREIGN PATENT DOCUMENTS

RU  2321363 C2 *  4/2008

OTHER PUBLICATIONS

RU 2321363 C2 English Translation obtained via Espacenet (Year: 2008).*

(Continued)

*Primary Examiner* — Katherine H Schwiker
*Assistant Examiner* — Zehra Jaffri
(74) *Attorney, Agent, or Firm* — Morgan, Lewis & Bockius LLP

(57) ABSTRACT

A method for closing a wound in a mucosal layer of an organ wall of a patient includes threading a suture thread into the mucosal layer at a first position located on a first side of the wound, threading the suture thread at least once into a muscle layer of the organ wall, and threading the suture thread into the mucosal layer at a second position located on a second side of the wound that is opposite the first side of the wound. A method for resecting a lesion in a wall of an organ of a patient includes creating a wound in a mucosal layer of the wall of the organ by excising the lesion from the wall of the organ, and threading a suture thread through a series passes between the mucosal layer on a first side of the wound and the mucosal layer on a second side of the wound, the suture thread being threaded into a muscle layer of the wall of the organ in at least one pass of the series passes.

20 Claims, 7 Drawing Sheets

(52) U.S. Cl.
CPC .............. *A61B 2017/00818* (2013.01); *A61B 2017/06176* (2013.01)

(58) Field of Classification Search
CPC ........... A61B 2017/06176; A61B 2017/00663; A61B 2017/00575; A61B 17/0057; A61B 2017/0027; A61B 2017/00637; A61B 2017/00641; A61F 5/0083; A61F 5/0086
See application file for complete search history.

(56) References Cited

U.S. PATENT DOCUMENTS

| | | | |
|---|---|---|---|
| 2015/0157358 A1* | 6/2015 | Mitelberg | A61B 17/32056 606/46 |
| 2016/0250056 A1* | 9/2016 | Keren | A61B 17/0491 606/144 |
| 2019/0290282 A1* | 9/2019 | Goto | A61B 17/1114 |
| 2019/0290325 A1* | 9/2019 | Goto | A61B 17/3478 |
| 2021/0022740 A1* | 1/2021 | Favreau | A61B 17/083 |

OTHER PUBLICATIONS

Goto, Osamu, et al. "A new endoscopic closure method for gastric mucosal defects: Feasibility of endoscopic hand suturing in an ex vivo porcine model (with video)." Endoscopy International Open, vol. 02, No. 02, Jun. 23, 2014, https://doi.org/10.1055/s-0034-1377180. (Year: 2014).*

* cited by examiner

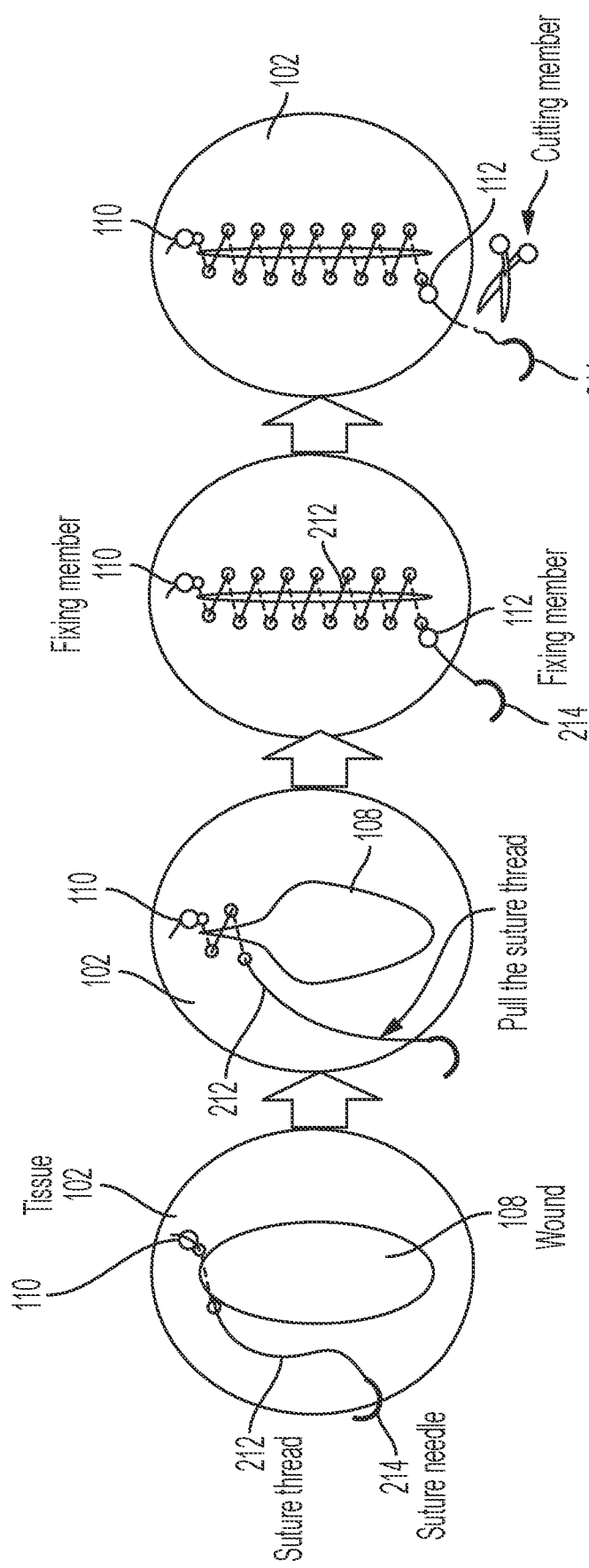

METHODS FOR CLOSING A WOUND

RELATED APPLICATION DATA

This application is based on and claims priority under 35 U.S.C. § 119 to U.S. Provisional Application No. 63/145,546, filed Feb. 4, 2021, the entire contents of which are incorporated herein by reference.

FIELD

The present disclosure, in certain embodiments, provides methods for resecting a lesion in a wall of an organ of a patient. In further embodiments, the present disclosure relates to methods for closing a wound. In some embodiments, methods of the present disclosure may be used to close wounds in the mucosal layer of a luminal organ of a patient. In some embodiments, methods of the present disclosure may be used to close wounds resulting from mucosectomy.

BACKGROUND

Mucosectomy is a surgical procedure that involves excising a portion of the mucous membrane from an organ of a patient, particularly along the gastrointestinal (GI) tract. Mucosectomy may be used, for example, to remove neoplasms, tumors, or other lesions from the internal wall of a luminal organ (e.g., esophagus, stomach, small intestine, colon, etc.). Two example mucosectomy techniques are endoscopic mucosal resection (EMR) and endoscopic submucosal dissection (ESD), each of which utilize endoscopy to excise lesions found along the GI tract. EMR may be used to remove lesions located near the wall surface in the mucosa layer, whereas ESD may be suitable for removing deeper lesions that have not extensively penetrated the muscle layer of the organ wall.

Methods for EMR and/or ESD can generally include elevating the lesion away from the muscle layer, followed by resection of the elevated lesion. In some instances, elevating the lesion away from the muscle layer is achieved by injecting a bolus of fluid (e.g., a saline solution) into the submucosa beneath the lesion sufficient to separate the lesion from the muscle layer. For certain EMR procedures, resection may include positioning and tightening a snare loop around the elevated lesion and resecting the strangulated lesion using, for example, electrocautery. For certain ESD procedures, resection of the lesion may include circumferential cutting of the surrounding mucosa of the lesion and dissection of the connective tissue of the submucosa beneath the lesion.

Whether by EMR, ESD, or other mucosectomy procedure, the resection of the lesion creates a wound in the mucosal and/or submucosal layers where the lesion has been removed. The wound may be left open and allowed to heal on its own, however, this route presents a risk of infection and/or bleeding, and may be an unacceptable option for certain patients, such as patients receiving antithrombotic drugs or blood thinning agents. Thus, in other instances, it may be desirable to close the wound.

For some procedures, surgical clips may be employed to close the wound. Surgical clips, however, are limited by their size and therefore may be suitable only for closing relatively small wounds. Wounds may alternatively be closed by suturing. Such suturing techniques may include, for example, passing a suture thread between the mucosal layer on opposing sides of the wound, and tightening the suture thread in order to draw the opposing sides together to close the wound. However, it has been found that typical suturing techniques may suffer from certain drawbacks.

SUMMARY

A difficulty that may arise from suturing the mucosal layers surrounding the wound is that a cavity may be formed between the muscle layer and the sutured mucosal layers. In some instances, the cavity may result because the muscle layer, which resists the compressive force of the suturing, deforms away from the mucosal layer as the opposing sides of the wound are drawn together by the suture thread. Generally, the size of the cavity will be proportional to the size of the wound. The presence of a large cavity can complicate healing of the wound since lymph fluids may accumulate in the cavity, and the cavity may become prone to infection. Furthermore, the presence of a significant cavity may also contribute to loosening of the suture thread over time since the underlying tissues can change shape and cause the suture thread to slacken.

The present disclosure, according to some embodiments, provides methods for closing a wound that can overcome the problems with known methods. In some embodiments, a method for closing a wound in a mucosal layer of an organ wall of a patient includes threading a suture thread into the mucosal layer at a first position located on a first side of the wound, threading the suture thread at least once into a muscle layer of the organ wall, and threading the suture thread into the mucosal layer at a second position located on a second side of the wound that is opposite the first side of the wound. The wound may be created by a mucosectomy procedure, for example, an EMR or ESD procedure.

In some embodiments, threading the suture thread into the muscle layer can help minimize or reduce the formation of a cavity between the mucosal layer and the muscle layer. In some embodiments, threading the suture thread into the muscle layer of the organ wall includes threading the suture thread into a portion of the muscle layer of the organ that is exposed by the wound. In some embodiments, the suture thread is threaded into a portion of the muscle layer that is centrally located between the first side and the second side of the wound. In some embodiments, the suture thread is threaded into the muscle layer only once. In other embodiments, the suture thread may be threaded into the muscle layer more than once. In some embodiments, the method further includes moving the first side of the wound toward the second side of the wound by pulling the suture thread. In some embodiments, pulling the suture thread further causes the muscle layer to move towards the mucosal layer.

In some embodiments, the present disclosure further provides a method for resecting a lesion in a wall of an organ of a patient. In some embodiments, a method for resecting the lesion includes creating a wound in a mucosal layer of the wall of the organ by excising the lesion from the wall of the organ, and threading a suture thread through a series passes between the mucosal layer on a first side of the wound and the mucosal layer on a second side of the wound. In some embodiments, a fluid is injected into the wall of the organ at a location proximate to the lesion prior to creating the wound. In some embodiments, the wound exposes a portion of a muscle layer located beneath the mucosal layer. In some embodiments, the wound extends into a submucosal layer between the mucosal layer and the muscle layer. In some embodiments, the suture thread is threaded into the muscle layer in at least one pass of the series passes. In some embodiments, threading the suture thread into the muscle layer includes threading the suture thread into the muscle layer at a location that is centrally located between the first side and the second side of the wound. In some embodiments, the suture thread is threaded into the exposed portion of the muscle in only one pass of the series passes, or at least one pass of the series passes. In some embodiments, the method further includes moving the first side of the wound toward the second side of the wound by pulling the suture thread. In some embodiments, pulling the suture thread further causes the muscle layer to move towards the mucosal layer.

The suture thread used in some or all of the embodiments described herein may be an absorbable suture thread. In some embodiments, the suture thread includes a plurality of barbs configured to anchor the suture thread in the muscle layer. The organ wall, in some embodiments, may be located in the GI tract of the patient (e.g., esophagus, stomach, colon, small intestine, etc.). In other embodiments, the organ wall may be a wall of a luminal organ of a different system, for example, organs of the respiratory system (e.g., trachea), circulatory system (e.g., veins or arteries), urinary tract (e.g., bladder), reproductive tract (e.g., uterus), etc. Furthermore, the methods described herein may be performed endoscopically (e.g., via an endoscope), according to some embodiments.

BRIEF DESCRIPTION OF THE DRAWINGS

The foregoing summary, as well as the following detailed description, will be better understood when read in conjunction with the appended drawings. For the purpose of illustrating the present disclosure, there are shown in the drawings embodiments which are presently preferred, wherein like reference numerals indicate like elements throughout. It should be noted, however, that aspects of the present disclosure can be embodied in different forms and thus should not be construed as being limited to the illustrated embodiments set forth herein. The elements illustrated in the accompanying drawings are not necessarily drawn to scale, but rather, may have been exaggerated to highlight the important features of the subject matter therein. Furthermore, the drawings may have been simplified by omitting elements that are not necessarily needed for the understanding of the disclosed embodiments.

FIGS. 2A-2D illustrate a suturing method for closing a wound created by resecting a lesion from the wall of an organ, according to certain embodiments.

DETAILED DESCRIPTION

The present subject matter will now be described more fully hereinafter with reference to the accompanying Figures, in which representative embodiments are shown. The present subject matter can, however, be embodied in different forms and should not be construed as limited to the embodiments set forth herein. Rather, these embodiments are provided to describe and enable one of skill in the art.

Figures 1A, 1B, 1C:
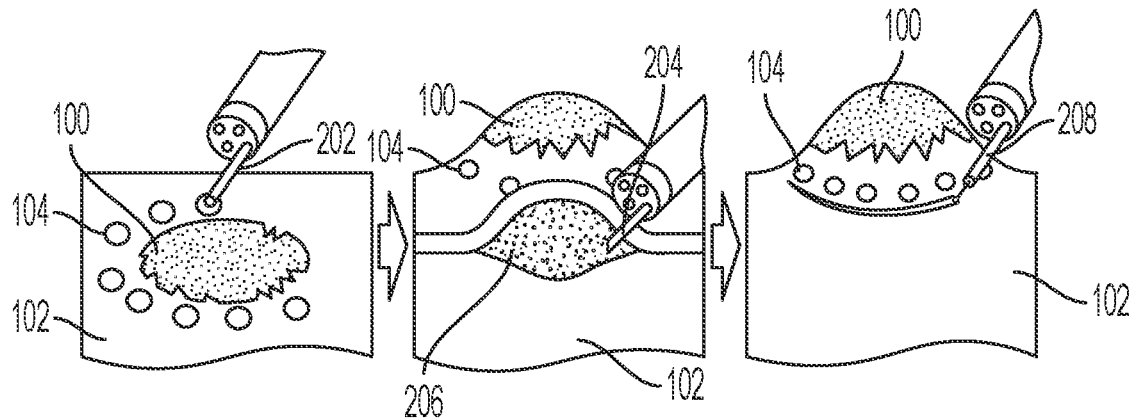
FIGS. 1A-1F illustrate steps for resecting a lesion from the wall of an organ of a patient according to certain example methods.

FIGS. 1A-1F illustrate steps of a mucosectomy procedure according to certain examples for resection of a lesion from an organ wall of a patient. The mucosectomy procedure may include, for example, an EMR procedure or an ESD procedure. The patient may be a human patient, or a non-human animal patient (e.g., a veterinarian patient). FIG. 1A shows a lesion 100 on a wall 102 of an organ of a patient, for example, a luminal organ of the GI tract (e.g., esophagus, stomach, small intestine, colon, etc.). Lesion 100 may be, for example, a benign tumor, cancerous tumor, or other abnormal growth that is present on the mucosa layer of wall 102. As further illustrated in FIG. 1A, a marking tool 202 (e.g., an endoscopic electric coagulator or cauterizer) may be used to create one or more markings 104 around lesion 100 in order to demarcate the boundary of lesion 100 for resection.

In FIG. 1B, an injection tool 204 (e.g. an endoscopic injection needle) is used to inject a fluid 206 into wall 102 beneath lesion 100. Fluid 206 may be an aqueous solution, for example, a saline solution or a hyaluronic acid solution. In some embodiments, fluid 206 is or includes a gel (e.g., hydrogels, thermogels, hydroxypropyl methylcellulose, poloxamer, etc.). Fluid 206 may further contain one or more pharmaceutically active agents (e.g., epinephrine). Fluid 206 may be injected into the submucosal layer of wall 102 beneath lesion 100, and may be injected through one or more injection sites around lesion 100. The amount of fluid 206 that is injected should be sufficient to elevate lesion 100 away from the muscle layer of wall 102 and cause lesion 100 to physically bulge from wall 102. In some embodiments, endoscopic images of lesion 100 and the surrounding tissue may be viewed to confirm sufficient elevation and bulging. The presence of wrinkles, for example, may indicate that bulging is insufficient and that additional fluid 206 may be needed. In some examples, about 40 mL to about 50 mL of fluid 206 may be administered via four or five syringes, each syringe containing about 10 mL of fluid 206. The amount of fluid 206 that is injected may be less or greater in other examples, depending on the size of lesion 100.

Figures 1D, 1E, 1F:
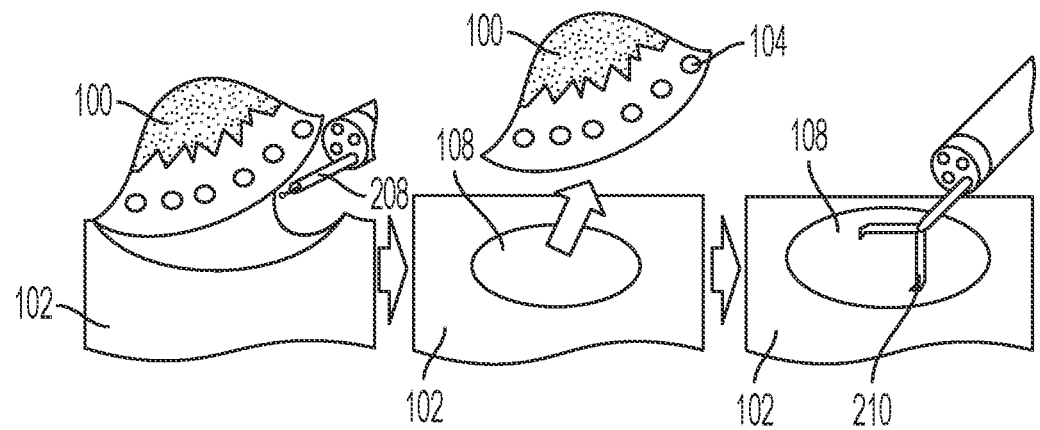

After lesion 100 is sufficiently elevated, lesion 100 may be excised from wall 102 as depicted in FIGS. 1C and 1D. A cutting tool 208 (e.g., an endoscopic electrosurgical knife) may be used to cut into the mucosal layer and/or submucosal layer of wall 102 around lesion 100. In some examples, cutting tool 208 is used to make a circumferential cut in the mucosal layer of wall 102 around the one or more markings 104. Dissection of connective tissues of the submucosa beneath lesion 100 may also be performed by cutting tool 208 in order to fully resect lesion 100 from wall 102.

FIG. 1E shows lesion 100 completely resected from wall 102. Lesion 100 may then be removed from the patient's body for pathological examination or disposal. The removal of lesion 100 leaves a wound 108 in wall 102 where lesion 102 was resected. Wound 108 may extend as deep as the mucosal layer or the submucosal layer of wall 102 according to some examples. Following removal of lesion 100, wound 108 may be closed to prevent bleeding, infection, or other complications. As shown in FIG. 1F, in some examples one or more surgical clips 210 may be employed to close wound 108. As discussed, surgical clips 210 may be suitable for wounds that are relatively small in size. Thus, in some embodiments, wound 108 may alternatively be closed by suturing with a suture thread, as depicted in FIGS. 2A-2D, for example.

As shown in FIG. 2A, a suture thread 212 is provided for closing wound 108. Suture thread 212, in some embodiments, may be an absorbable suture thread and have a gauge of USP 3-0 or about 0.2 mm diameter, for example. In some embodiments, suture thread 212 may be a barbed suture thread. At a first end of suture thread 212 is a suture needle 214 for piercing the mucosal layer of wall 102 and guiding suture thread 212 there through.

Suture needle 214 may be, for example, a curved needle and may be manipulated by an endoscopic needle holder or forceps (not shown). A second end of suture thread 212 may be anchored in wall 102 at a first location 110 proximate to wound 108, for example, by one or more knots. In some embodiments, second end of suture thread 212 may include an eyelet through which suture needle 214 and the first end of suture thread 212 may be passed to form a loop for anchoring around a portion of the mucosa at first location 110.

To suture wound 108, in some embodiments, suture thread 212 is passed through the mucosal layer of wall 102 back and forth between opposite sides of wound 108 beginning from location 110, as illustrated in FIGS. 2B and 2C. Suture thread 212 may then be pulled tight to draw the opposing sides of wound 108 closed, and suture thread 212 may be anchored at a second location 112 in wall 102, e.g., by one or more knots, in order to prevent suture thread 212 from backing out. In some embodiments, wound 108 may be closed with a continuous stitch. In other embodiments, wound 108 may be closed by a series of separate stitches. Once the suturing is completed, suture needle 214 may be detached from suture thread 212, for example, by cutting suture thread 212 with a cutting tool (e.g., endoscopic cutting forceps) at a location between suture needle 214 and second location 112, as shown in FIG. 2D.

Figure 3A:
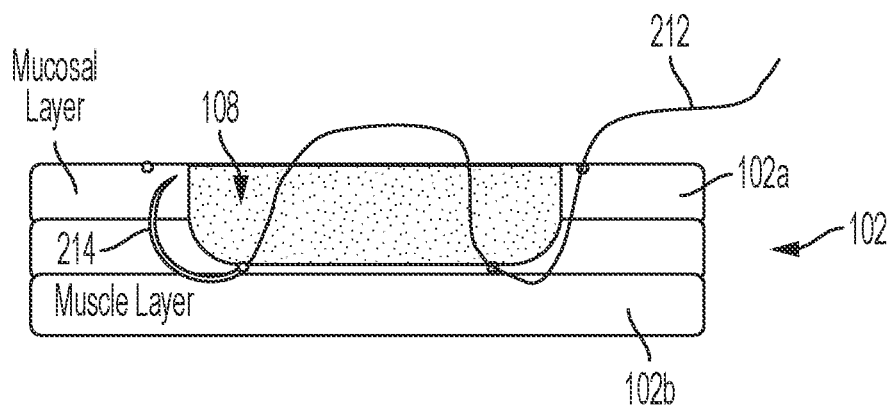
FIGS. 3A and 3B are partial sectional views illustrating the closing of the mucosal layers surrounding a wound using a suture thread, and the formation of a cavity underneath the sutured mucosal layers, according to certain embodiments.
Figure 3B:
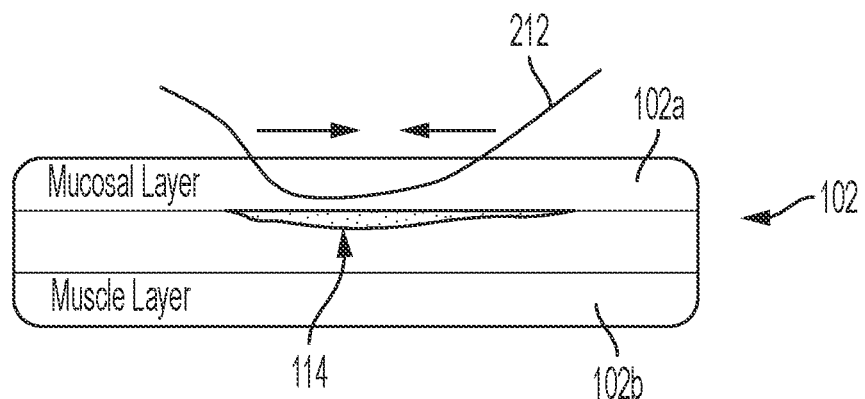

As discussed, a problem that may be encountered is that a cavity forms between the sutured mucosa layer and the underlying muscle layer. An example is illustrated in FIGS. 3A and 3B. FIG. 3A illustrates a sectional view of wall 102 having wound 108 in mucosal layer 102a. Wound 108 may extend through the depth of mucosal layer 102a toward muscle layer 102b. In some examples, wound 108 may extend into a submucosal layer between mucosal layer 102a and muscle layer 102b. Suture thread 212, with suture needle 214, is threaded through mucosal layer 102a on a first side of wound 108, extends across a length of wound 108, and is threaded through mucosal layer 102a on a second side of wound 108. By pulling suture thread 212 tight, the mucosal layer 102a on opposing first and second sides of wound 108 can be drawn together to close wound 108, as shown in FIG. 3B. However, because muscle layer 102b may resist the compressive force of suture thread 212, muscle layer 102b may deform away from mucosal layer 102a, resulting in a cavity 114 beneath the sutured mucosal layer 102a.

Figure 4A:
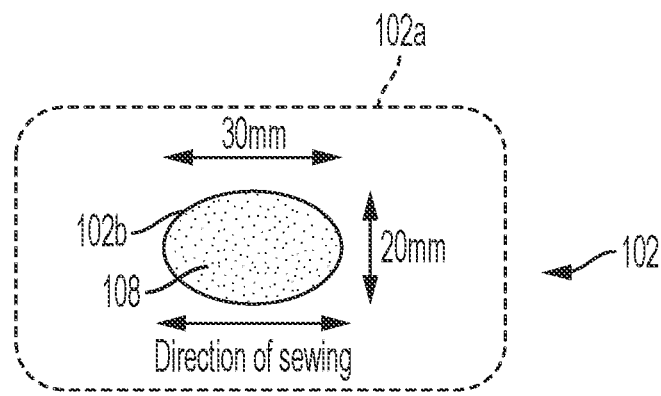
FIGS. 4A-4C illustrate the closing of the mucosal layers surrounding a wound using a suture thread, and the formation of a cavity underneath the sutured mucosal layers, according to certain embodiments.
Figure 4B:
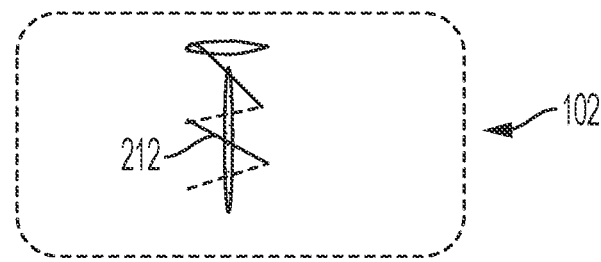
Figure 4C:
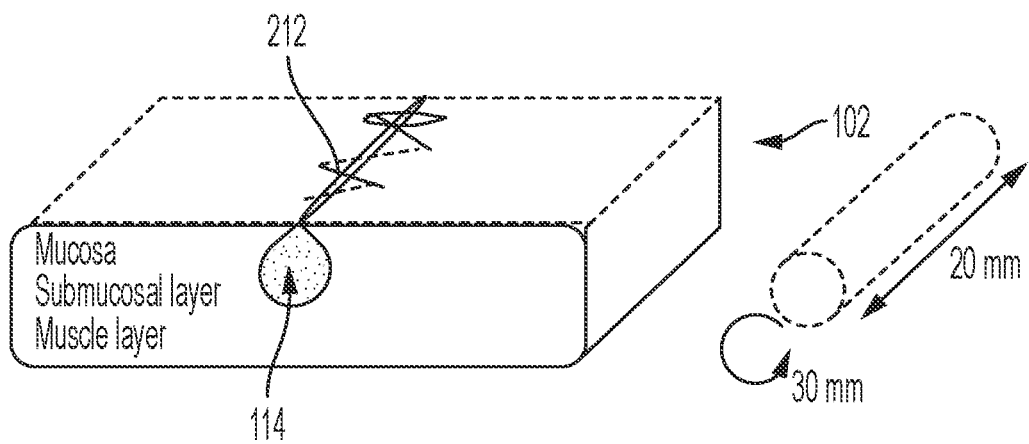

The volume of cavity 114 can be proportional to the size of wound 108 such that larger wounds may result in larger cavities after suturing. In some cases, a wound 108 having a length L and width W may result in a cavity with a volume that can be roughly approximated by a cylinder of circumference L and height W and a volume $V=W\ \pi[L/(2\pi)]^2$. FIGS. 4A-4C illustrate one such example. FIG. 4A shows a plan view of wound 108 in a wall 102 prior to suturing, wound 108 having a length of about 30 mm and a width of about 20 mm. FIG. 4B is a further plan view showing wound 108 closed after the mucosal layer on opposing sides of the length of wound 108 have been drawn together by suture thread 212. FIG. 4C is a perspective sectional view showing cavity 114 between the muscle layer of wall 102 and the sutured mucosal layer. In this example, the volume of cavity 114 can be approximated by a cylinder having a circumference of 30 mm and a height of 20 mm which has a volume $V=(20\ \text{mm})\ \pi[(30\ \text{mm})/(2\pi)]^2$ or about 1.4 cm$^3$.

The presence of a large cavity 114 can complicate healing of wound 108. For example, lymph fluids may accumulate in cavity 114, and cavity 114 may become susceptible to infection. Furthermore, cavity 114 may also contribute to loosening of suture thread 212 over time since the underlying tissues may be prone to changing shape and cause suture thread 212 to slacken. Accordingly, certain embodiments of the present disclosure provide methods for decreasing or minimizing the size of cavity 114. In some embodiments, for example, the size of cavity 114 may be decreased by passing suture thread 212 at least once through a portion of the underlying muscle layer in order to pull the muscle layer toward the mucosal layer during suturing.

Figure 5A:
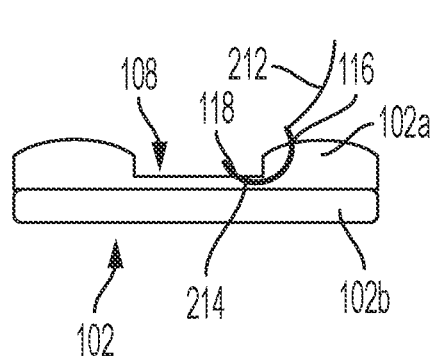
FIGS. 5A-5E are partial sectional views illustrating steps of a method for closing a wound using a suture thread where the suture thread is passed through a portion of the muscle layer, according to certain embodiments.
Figure 5B:
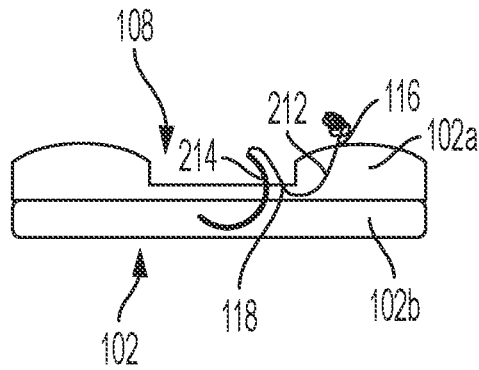
Figure 5C:
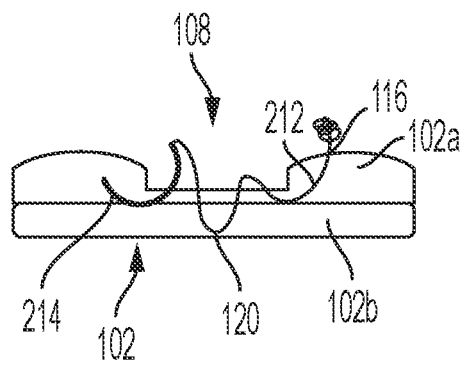
Figure 5D:
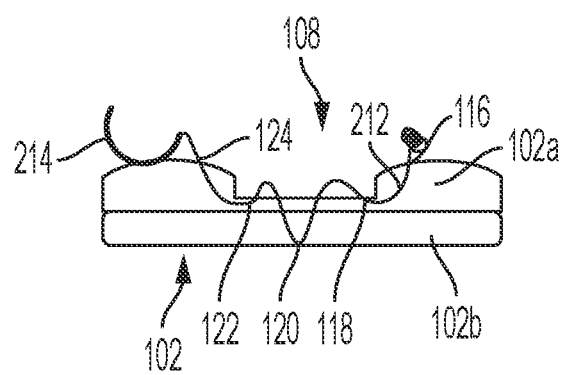
Figure 5E:
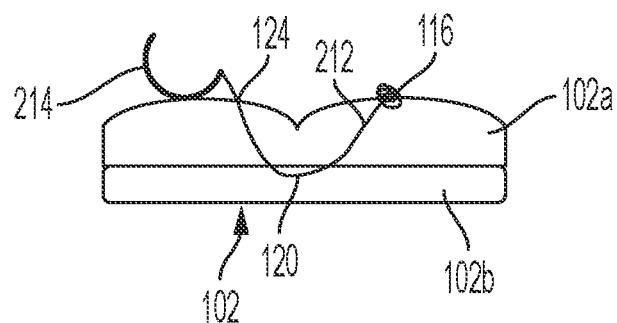

FIGS. 5A-5E are sectional views that illustrate a method for closing wound 108 according to certain embodiments of the present disclosure. In FIG. 5A, suture needle 214 and suture thread 212 are threaded into wall 102 at a first location (e.g., location 116) on a first side of wound 108. First location 116 may be on the mucosal layer 102a of wall 102. In some embodiments, suture needle 214 and suture thread 212 exit at a second location (e.g., location 118) proximate an edge of wound 108 on the first side of wound 108. Location 118 may be on the mucosal layer 102a or, in some embodiments, a submucosal layer between mucosal layer 102a and muscle layer 102b. As shown in FIGS. 5B and 5C, suture needle 214 and suture thread 212 are further threaded, at least once, into and out of muscle layer 102b at a third location (e.g., location 120). In some embodiments, suture needle 214 and suture thread 212 are threaded into a portion of muscle layer 102b that was exposed when wound 108 was created. Location 120, in some embodiments, may be at or proximate a center of wound 108. After being threaded into muscle layer 102b, in some embodiments, suture needle 214 and suture thread 212 is threaded into the mucosal layer 102a on a second side of wound 108 that is opposite of the first side. In some embodiments, suture needle 214 and suture thread 212 are threaded through a fourth location (e.g., location 122) that may be proximate an edge of wound 108 on the second side of wound 108 and exit wall 102 at a fifth location (e.g., location 124), as shown in FIG. 5D. Location 124 may be on the mucosal layer 102a of wall 102 on the second side of wound 108. To close wound 108, suture thread 212 may be pulled tight to draw the opposing first and second sides of wound 108 together, as depicted in FIG. 5E. In some embodiments, because suture thread 212 is threaded through a portion of muscle layer 102b, muscle layer 102b may be pulled towards the sutured mucosal layer 102a, thus avoiding or at least reducing the size of any cavity that forms between mucosal layer 102a and muscle layer 102b.

Figure 6A:
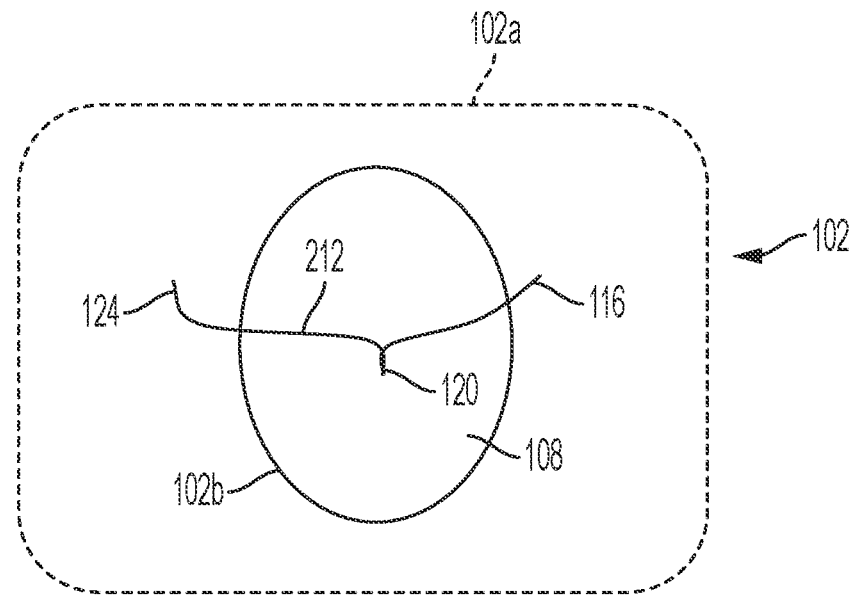
FIGS. 6A and 6B are plan views that each illustrate a suture thread threaded between the mucosal layer on a first side of a wound to the mucosal layer on a second side of the wound, the suture thread being threaded through a portion of the muscle layer centrally located between the first side and the second side, according to certain embodiments.
Figure 6B:
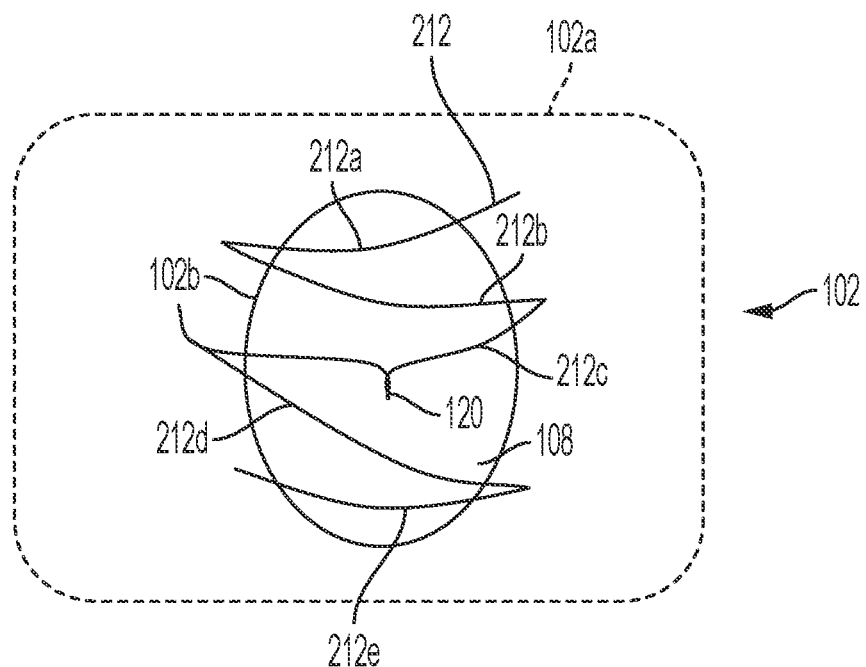

FIG. 6A is a plan view according to some embodiments showing wound 108 in wall 102 and suture thread 212 threaded into the exposed muscle layer 102b within wound 108 prior to wound 108 being closed. More particularly, suture thread 212 is threaded into mucosal layer 102a on a first side of wound 108 (e.g., at location 116), threaded into muscle layer 102b at or proximate to the center of wound 108 (e.g., at location 120), and then threaded into mucosal layer 102a on a second side of wound 108 (e.g., at location 124) that is opposite the first side. In some embodiments, suture thread 212 may make multiple passes (e.g., 212a, 212b, 212c, 212d, 212e) between the mucosal layer 102a on first side and second side of wound 108, as shown in FIG. 6B. The multiple passes may include substantially parallel passes, substantially non-parallel passes, and combinations thereof. In some embodiments, at least one of the passes of suture thread 212 is threaded into muscle layer 102b (e.g., 212c at location 120). In some embodiments, passes of suture thread 212 that are not threaded into muscle layer 102b are threaded only through the mucosal layer 102a and/or submucosal layer on either sides of wound 108. In some embodiments, only one of the passes of suture thread 212 is threaded into muscle layer 102b. In other embodiments, each of the passes of suture thread 212 is threaded into muscle layer 102b.

Figure 7A:
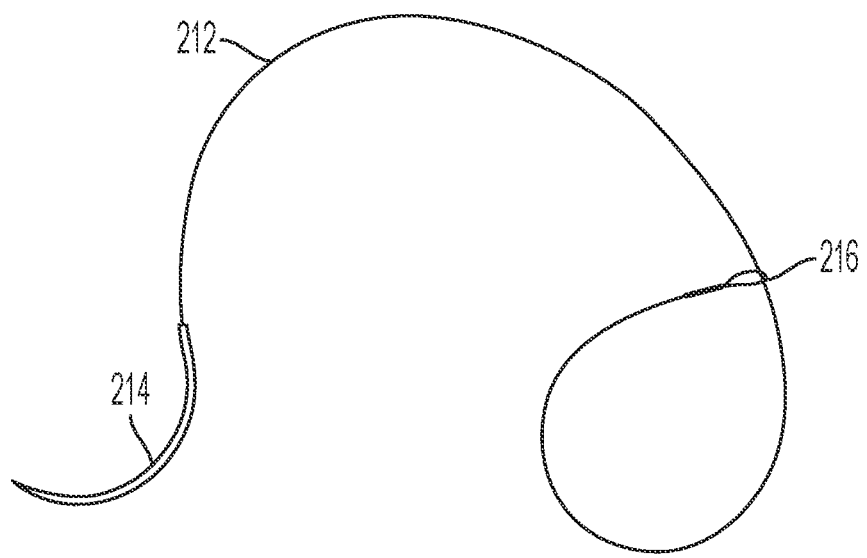
FIGS. 7A and 7B are photographs showing an example suture and suture needle that may be used according to certain embodiments.
Figure 7B:
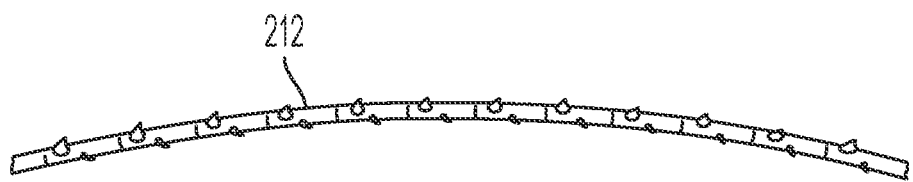

FIGS. 7A and 7B show an example suture thread 212 and suture needle 214 that may be used in accordance with some or each of the embodiments of the present disclosure. Suture thread 212 may be made from an bio-absorbable material and, in some embodiments, may include a plurality of barbs (visible in FIG. 7B) that are configured to help anchor suture thread 212 in wall 102 (e.g., in muscle layer 102b and/or mucosal layer 102a) and reduce or eliminate the need for tying knots to secure suture thread 212 in wall 102. For example, the barbs of suture thread 212 may help anchor suture thread 212 in the muscle layer (e.g., muscle layer 102b) without the need for any knots to be tied in the muscle layer. In further embodiments, suture thread 212 may include an eyelet 216 at the end opposite of suture needle 214. In some such embodiments, suture needle 214 may be passed through eyelet 216 to form a loop that may be used for anchoring suture thread 212 to wall 102.

While certain embodiments of the present disclosure have been described in connection with certain EMR or ESD procedures, the methods and devices described herein are not necessarily limited to these procedures. Methods and devices according to some embodiments that are useful for closing wounds may be adapted for use with other mucosectomy procedures or other medical procedures which result in a wound. Furthermore, the methods and devices described herein are not necessarily limited for use in the GI tract of a patient, and may be adapted for use in other luminal organs, for example, organs of the respiratory system (e.g., trachea), circulatory system (e.g., veins or arteries), urinary tract (e.g., bladder), reproductive tract (e.g., uterus), etc.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, composition of matter, means, methods, or steps, presently existing or later to be developed that perform substantially the same function or achieve substantially the same result as the corresponding embodiments described herein may be used according to the present disclosure.

What is claimed is:

1. A method for closing a wound in a mucosal layer of a luminal organ wall of a patient, the method comprising:
    passing a suture thread through the mucosal layer at a first position located on a first side of the wound, the suture thread exiting the mucosal layer at a second position proximate an edge of the wound on the first side of the wound;
    inserting the suture thread into an exposed surface of a muscle layer to a third position within the muscle layer and turning the suture thread within the muscle layer such that the suture thread exits out of the exposed surface of the muscle layer, wherein the exposed surface of the muscle layer is exposed toward an interior of the luminal organ by resecting a section of the mucosal layer from the muscle layer; and
    passing the suture thread through the mucosal layer at a fourth position located on a second side of the wound that is opposite the first side of the wound, wherein a portion of the suture thread between the first position and the fourth position is within the muscle layer.

2. The method of claim 1, wherein the third position within the muscle layer is centrally located between the first side and the second side of the wound.

3. The method of claim 1, wherein the suture thread comprises a plurality of barbs configured to anchor the suture thread in the muscle layer.

4. The method of claim 1, wherein the wound does not extend through an entire thickness of the luminal organ wall.

5. The method of claim 1, wherein the suture thread does not pass through an entire thickness of the muscle layer.

6. The method of claim 1, further comprising moving the first side of the wound toward the second side of the wound while lifting the muscle layer towards the mucosal layer by pulling the suture thread.

7. The method of claim 1, wherein the exposed surface of the muscle layer extends perpendicular to a thickness of the wall of the luminal organ at the exposed surface.

8. The method of claim 1, further comprising pulling the suture thread to lift the exposed surface of the muscle layer toward the interior of the luminal organ to reduce a space between the mucosal layer and the muscular layer; wherein the mucosal layer on the first side of the wound and the mucosal layer on the second side of the wound are sutured together with the exposed surface of the muscle layer that is lifted toward the interior of the luminal organ.

9. The method of claim 1, further comprising pulling the suture thread to lift the exposed surface of the muscle layer toward the first and second position to reduce a space between the mucosal layer and the muscle layer.

10. A method for closing a wound of a luminal organ of a patient, the method comprising:
    creating a wound in a mucosal layer of a wall of the luminal organ by excising a lesion from the wall of the luminal organ, wherein excising the lesion exposes a surface of a muscle layer of the wall of the luminal organ beneath the lesion, the exposed surface of the muscle layer facing towards an interior of the luminal organ; and
    passing a suture thread through a series of passes between the mucosal layer on a first side of the wound and the mucosal layer on a second side of the wound, wherein in at least one pass of the series of passes the suture thread is inserted through a position on the exposed surface of the muscle layer to a location within the muscle layer and turned within the muscle layer to exit out of the exposed surface of the muscle layer at another position, wherein a portion of the suture thread between the mucosal layer on a first side of the wound and the mucosal layer on a second side of the wound is within the muscle layer.

11. The method of claim 10, wherein the location within the muscle layer is centrally located between the first side and the second side of the wound.

12. The method of claim 10, wherein the suture thread is inserted into the exposed surface of the muscle layer in only one pass of the series passes.

13. The method of claim 10, wherein the exposed surface of the muscle layer extends perpendicular to a thickness of the wall of the luminal organ at the exposed surface.

14. The method of claim 10, further comprising pulling the suture thread to lift the exposed surface of the muscle layer toward the interior of the luminal organ to reduce a space between the mucosal layer and the muscular layer; wherein the mucosal layer on the first side of the wound and the mucosal layer on the second side of the wound are sutured together with the exposed surface of the muscle layer that is lifted toward the interior of the luminal organ.

15. The method of claim 10, further comprising pulling the suture thread to lift the exposed surface of the muscle layer toward the first and second sides of the wound to reduce a space between the mucosal layer and the muscle layer.

16. A method for closing a wound of a luminal organ of a patient, the method comprising:
   creating an exposed surface of a muscle layer by excising a portion of a mucosal layer of a wall of the luminal organ, the exposed surface of the muscle layer facing towards an interior of the luminal organ;
   passing a suture thread through the mucosal layer around the exposed surface of the muscle layer; and
   inserting the suture thread through a position on the exposed surface of the muscle layer to a location within the muscle layer and turning the suture thread within the muscle layer such that the suture thread exits out of the exposed surface of the muscle layer at another position, wherein a portion of the suture thread is within the muscle layer.

17. The method of claim 16, wherein the suture thread is an absorbable suture thread.

18. The method of claim 16, wherein the suture thread does not pass through an entire thickness of the muscle layer.

19. The method of claim 16, wherein the exposed surface of the muscle layer extends perpendicular to a thickness of the wall of the luminal organ at the exposed surface.

20. The method of claim 16, further comprising pulling the suture thread to lift the exposed surface of the muscle layer toward the edge of the wound to reduce a space between the mucosal layer and the muscle layer.

* * * * *